US008812258B2

(12) United States Patent
Nadkarni et al.

(10) Patent No.: US 8,812,258 B2
(45) Date of Patent: *Aug. 19, 2014

(54) IDENTIFYING A TYPE OF MOTION OF AN OBJECT

(71) Applicants: Vijay Nadkarni, San Jose, CA (US); Jeetendra Jangle, Fremont, CA (US); John Bentley, Santa Clara, CA (US); Umang Salgia, Nigadi (IN)

(72) Inventors: Vijay Nadkarni, San Jose, CA (US); Jeetendra Jangle, Fremont, CA (US); John Bentley, Santa Clara, CA (US); Umang Salgia, Nigadi (IN)

(73) Assignee: Numera, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,170

(22) Filed: Aug. 23, 2013

(65) Prior Publication Data
US 2013/0346014 A1 Dec. 26, 2013

Related U.S. Application Data

(63) Continuation of application No. 12/883,304, filed on Sep. 16, 2010, now Pat. No. 8,560,267, which is a continuation-in-part of application No. 12/560,069, filed on Sep. 15, 2009, now abandoned.

(60) Provisional application No. 61/208,344, filed on Feb. 23, 2009.

(51) Int. Cl.
G01C 22/00 (2006.01)
G06K 9/00 (2006.01)
G06F 19/00 (2011.01)
A61B 5/11 (2006.01)
A61B 5/00 (2006.01)

(52) U.S. Cl.
CPC .......... *G01C 22/006* (2013.01); *G06K 9/00342* (2013.01); *G06F 19/345* (2013.01); *A61B 5/1116* (2013.01); *A61B 5/726* (2013.01)
USPC .............. 702/160; 702/19; 702/141; 702/161

(58) Field of Classification Search
CPC ................. G01C 21/16; G01C 22/006; A61B 2562/0219; A63B 69/0028
USPC .............. 702/19, 141, 160–161; 73/489–490, 73/492, 510, 865.4
See application file for complete search history.

(56) References Cited

U.S. PATENT DOCUMENTS 4,513,437 A  4/1985  Chainer et al.
6,028,626 A  2/2000  Aviv
(Continued)

OTHER PUBLICATIONS

Response to Office Action submitted Jan. 23, 2011, for U.S. Appl. No. 12/560,069, filed Sep. 15, 2009.

(Continued)

*Primary Examiner* — Elias Desta
(74) *Attorney, Agent, or Firm* — Brian R Short

(57) ABSTRACT

An apparatus for identifying a type of motion and condition of a user is disclosed. One apparatus includes a motion detection sensor operative to generate an acceleration signature based on sensed acceleration of the user, and a controller. The controller is operative to determine what network connections are available to the motion detection device, match the acceleration signature with at least one of a plurality of stored acceleration signatures, wherein each stored acceleration signatures corresponds with a type of motion of the user, wherein the apparatus distributes at least some of the acceleration signature matching processing when processing capability is available to the motion detection device though available network connections, and identify the type of motion of the user and identify a condition of the user based on the matching of the acceleration signature.

20 Claims, 9 Drawing Sheets

(56) References Cited

U.S. PATENT DOCUMENTS

| | | |
|---|---|---|
| 6,265,982 B1 | 7/2001 | Ostwald |
| 6,626,728 B2 | 9/2003 | Holt |
| 6,675,649 B2 | 1/2004 | Uchiyama et al. |
| 6,756,889 B2 | 6/2004 | Sala et al. |
| 6,802,814 B2 | 10/2004 | Narimatsu |
| 6,816,766 B2 | 11/2004 | Sala et al. |
| 6,999,863 B2 | 2/2006 | Neal et al. |
| 7,145,461 B2 | 12/2006 | Lehrman et al. |
| 7,248,172 B2 | 7/2007 | Clifford et al. |
| 7,467,060 B2 | 12/2008 | Kulach et al. |
| 7,715,982 B2 | 5/2010 | Grenfell et al. |
| 7,827,000 B2 | 11/2010 | Stirling et al. |
| 7,881,902 B1 * | 2/2011 | Kahn et al. .................. 702/160 |
| 8,060,337 B2 | 11/2011 | Kulach et al. |
| 8,560,267 B2 * | 10/2013 | Jangle et al. ................. 702/160 |
| 2003/0158489 A1 | 8/2003 | Narimatsu |
| 2005/0154512 A1 | 7/2005 | Schubert et al. |
| 2006/0005578 A1 | 1/2006 | Tortoli |
| 2006/0089538 A1 | 4/2006 | Cuddihy et al. |
| 2006/0282021 A1 | 12/2006 | DeVaulet al. |
| 2007/0167693 A1 | 7/2007 | Scholler et al. |
| 2007/0293781 A1 | 12/2007 | Sims et al. |
| 2008/0256796 A1 | 10/2008 | Fix |
| 2009/0303204 A1 | 12/2009 | Nasiri et al. |
| 2010/0073284 A1 | 3/2010 | Dods et al. |
| 2010/0121226 A1 | 5/2010 | Ten Kate et al. |
| 2010/0217533 A1 | 8/2010 | Nadkarni et al. |

OTHER PUBLICATIONS

Response to Office Action submitted Apr. 2, 2013, for U.S. Appl. No. 12/621,099, filed Nov. 18, 2009.

Response to Office Action submitted May 10, 2012, for U.S. Appl. No. 12/883,304, filed Sep. 16, 2010.

\* cited by examiner

Slow Falling and lying down summersault

Slipping and falling on back on a bouncy surface (air mattress)

IDENTIFYING A TYPE OF MOTION OF AN OBJECT

RELATED APPLICATIONS

This patent application is a continuation of U.S. patent application Ser. No. 12/883,304, filed Sep. 16, 2010, which is a continuation in part (CIP) of U.S. patent application Ser. No. 12/560,069 filed on Sep. 15, 2009, which claims priority to U.S. provisional patent application Ser. No. 61/208,344 filed on Feb. 23, 2009 which are all incorporated by reference.

FIELD OF THE DESCRIBED EMBODIMENTS

The described embodiments relate generally to motion detecting. More particularly, the described embodiments relate to a method and apparatus for identifying a type of motion of an animate or inanimate object.

BACKGROUND

There is an increasing need for remote monitoring of individuals, animals and inanimate objects in their daily or natural habitats. Many seniors live independently and need to have their safety and wellness tracked. A large percentage of society is fitness conscious, and desire to have, for example, workouts and exercise regimen assessed. Public safety officers, such as police and firemen, encounter hazardous situations on a frequent basis, and need their movements, activities and location to be mapped out precisely.

The value in such knowledge is enormous. Physicians, for example, like to know their patients sleeping patterns so they can treat sleep disorders. A senior living independently wants peace of mind that if he has a fall it will be detected automatically and help summoned immediately. A fitness enthusiast wants to track her daily workout routine, capturing the various types of exercises, intensity, duration and caloric burn. A caregiver wants to know that her father is living an active, healthy lifestyle and taking his daily walks. The police would like to know instantly when someone has been involved in a car collision, and whether the victims are moving or not.

Existing products for the detection of animate and inanimate motions are simplistic in nature, and incapable of interpreting anything more than simple atomic movements, such as jolts, changes in orientation and the like. It is not possible to draw reliable conclusions about human behavior from these simplistic assessments.

It is desirable to have an apparatus and method that can accurately monitor motion of either animate of inanimate objects.

SUMMARY

An embodiment includes a method of detecting human condition and activity of a user. The method includes generating, by a motion detection device that includes a motion detection sensor, an acceleration signature based on sensed acceleration of an object that represents motion of the user, the motion detection device determining what network connections are available to the motion detection device, matching the acceleration signature with at least one of a plurality of stored acceleration signatures of motions of human beings, wherein each stored acceleration signatures corresponds with a type of motion, wherein the motion detection device distributes at least some of the acceleration signature matching processing when processing capability is available to the motion detection device though available network connections, and identifying a type of motion of the user and identifying a condition of the user based on the matching of the acceleration signature with a stored acceleration signature.

Another embodiment includes an apparatus for identifying a type of motion and condition of a user. The apparatus includes a motion detection sensor operative to generate an acceleration signature based on sensed acceleration of the user, and a controller. The controller is operative to determine what network connections are available to the motion detection device, match the acceleration signature with at least one of a plurality of stored acceleration signatures, wherein each stored acceleration signatures corresponds with a type of motion of the user, wherein the apparatus distributes at least some of the acceleration signature matching processing when processing capability is available to the motion detection device though available network connections, and identify the type of motion of the user and identify a condition of the user based on the matching of the acceleration signature.

Other aspects and advantages of the described embodiments will become apparent from the following detailed description, taken in conjunction with the accompanying drawings, illustrating by way of example the principles of the described embodiments.

DETAILED DESCRIPTION

Figure 1:
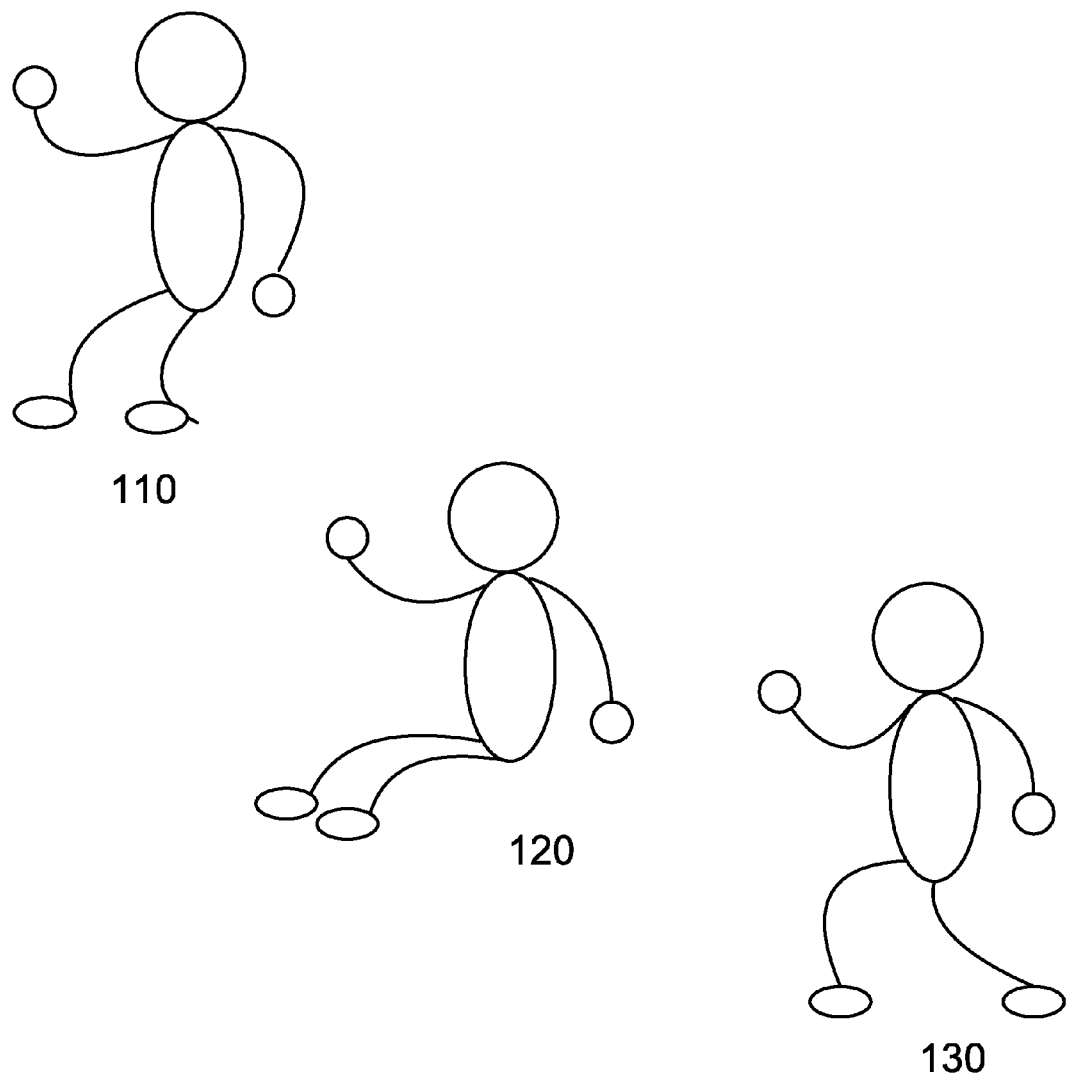
FIG. 1 shows examples of different types of motions of a human being that an object attached to the human being can be used to detect or sense.

The monitoring of human activities generally falls into three categories: safety, daily lifestyle, and fitness. By carefully interpreting human movements it is possible to draw accurate and reasonably complete inferences about the state of well being of individuals. A high degree of sophistication is required in these interpretations. Simplistic assessments of human activity lead to inaccurate determinations, and ultimately are of questionable value. By contrast, a comprehensive assessment leads to an accurate interpretation and can prove to be indispensable in tracking the well being and safety of the individual.

To draw accurate inferences about the behavior of humans, it turns out that the atomic movements become simply alphabets that include elemental motions. Furthermore, specific sequences of elemental motions become the vocabulary that comprises human behavior. As an example, take the case of a person who leaves the home and drives to the shopping center. In such a scenario, the behavioral pattern of the person is walking to the door or the house, opening and closing the door, walking further to the car, settling down in the car, starting the engine, accelerating the car, going through a series of stops, starts and turns, parking the car, getting out and closing the car door, and finally walking to the shopping center. This sequence of human behavior is comprised of individual motions such as standing, walking, sitting, accelerating (in the car), decelerating, and turning left or right. Each individual motion, for example walking, is comprised of multiple atomic movements such as acceleration in an upward direction, acceleration in a downward direction, a modest forward acceleration with each step, a modest deceleration with each step, and so on.

With written prose, letters by themselves convey almost no meaning at all. Words taken independently convey individual meaning, but do not provide the context to comprehend the situation. It takes a complete sentence to obtain that context. Along the same line of reasoning, it requires a comprehension of a complete sequence of movements to be able to interpret human behavior.

Although there is an undeniable use for products that are able to detect complex human movements accurately, the key to the success of such technologies lies in whether users adopt them or not. The technology needs to capture a wide range of human activities. The range of movements should ideally extend to all types of daily living activities that a human being expects to encounter—sleeping, standing, walking, running, aerobics, fitness workouts, climbing stairs, vehicular movements, falling, jumping and colliding, to name some of the more common ones.

It is important to detect human activities with a great deal of precision. In particular, activities that relate to safety, fitness, vehicular movements, and day to day lifestyle patterns such as walking, sleeping, climbing stairs, are important to identify precisely. For example, it is not enough to know that a person is walking One needs to know the pace and duration of the walk, and additional knowledge of gait, unsteadiness, limping, cadence and the like are important.

It is critical that false positives as well as false negatives be eliminated. This is especially important for cases of safety, such as falls, collisions, and the like. Human beings come in all types—short, tall, skinny, obese, male, female, athletic, couch potato, people walking with stick/rolator, people with disabilities, old and young. The product needs to be able to adapt to their individuality and lifestyle.

The embodiments described provide identification of types of motion of an animate or inanimate object. Motion is identified by generating acceleration signatures based on the sensed acceleration of the object. The acceleration signatures are compared with a library of motion signature, allowing the motion of the object to be identified. Further, sequences of the motions can be determined, allowing identification of activities of, for example, a person the object is attached to.

Just as the handwritten signatures of a given human being are substantively similar from one signature instance to the next, yet have minor deviations with each new instance, so too will the motion signatures of a given human be substantively similar from one motion instance to the next, yet have minor deviations.

Algorithms used for pattern recognition (signature matching) should have the sophistication to accurately handle a wide range of motions. Such algorithms should have the ability to recognize the identical characteristics of a particular motion by a given human being, yet allow for minor variations arising from human randomness. Additionally, the devices used to monitor peoples' movement need to be miniature and easy to wear. These two objectives are fundamentally opposed. However, the described embodiments provide a single cohesive system that is both sophisticated enough to detect a wide range of motions.

FIG. 1 shows examples of different types of motions of a human being that an object attached to the human being can be used to detect or sense. The human motions can include, for example, standing, sleeping, walking, and running A first motion 110 can include walking A second motion 120 can include falling. A third motion 130 can include running Each of the motions generates a unique motion signature. As will be described, the signatures can be universal to, for example, many individuals. Additionally, the signatures can have additional characteristics that are unique to an individual.

Figure 2A:
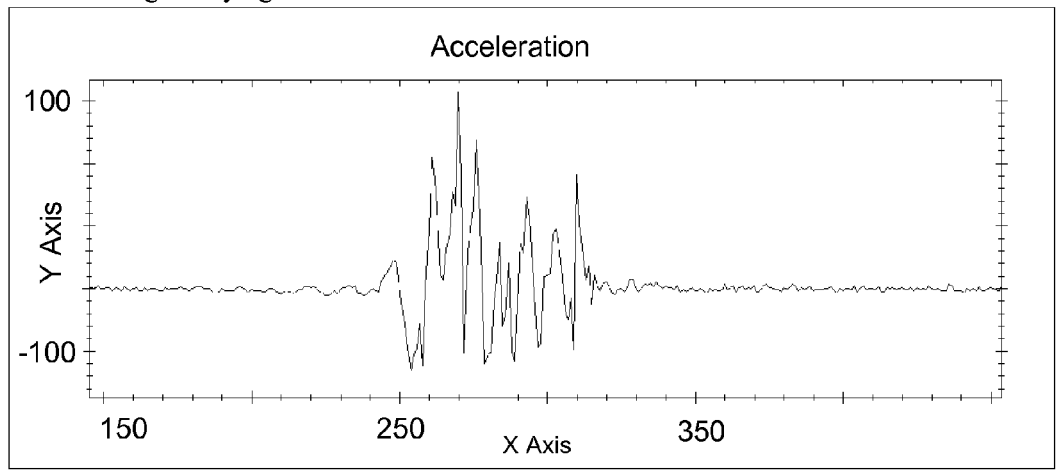
FIGS. 2A, 2B, 2C shows examples of time-lines of several different acceleration curves (signatures), wherein each signature is associated with a different type of sensed or detected motion.
Figure 2B:
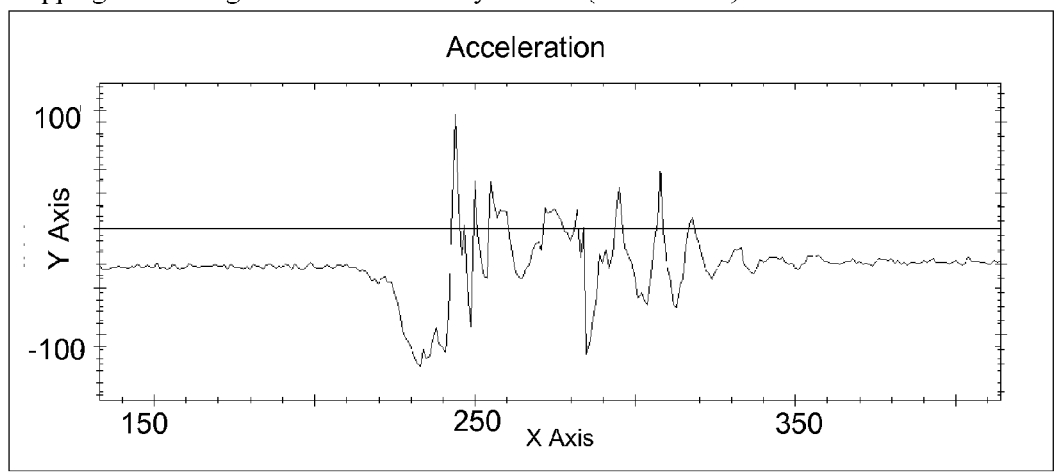
Figure 2C:
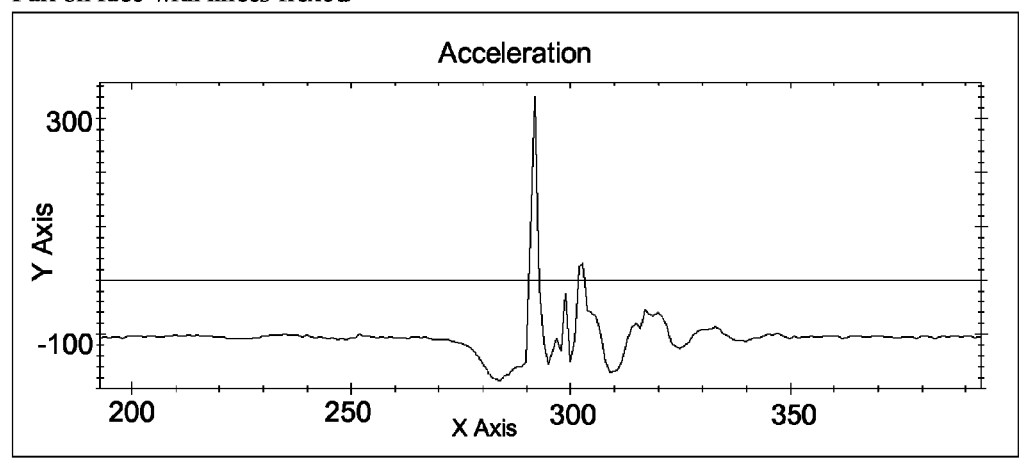

FIGS. 2A, 2B, 2C shows examples of different types of acceleration and orientation signatures for various sample motions by human beings. It should be noted that these signatures are expected to have certain components that are common from one human being to the next, but also have certain components that vary from one human to the next.

The signatures of FIGS. 2A, 2B, 2C are depicted in only one orientation. That is, three accelerometers can be used to generate acceleration signatures in the X, Y and Z (three) orientations. The signatures of FIGS. 2A, 2B, 2C only show the signature of one of the three orientations. It is to be understood that matching can use the other orientations as well.

FIG. 2A shows an example of an acceleration signature of a person doing a slow fall and lying down summersault. FIG. 2B shows an example of an acceleration signature of a person slipping and falling back on a bouncy surface (for example, an air mattress). FIG. 2C shows an acceleration signature of a person fall on their face with their knees flexed. By matching an acceleration signature that has been generated by sensing the motion of a person with one of many stored signatures, the motion of the person can be determined.

Figure 3:
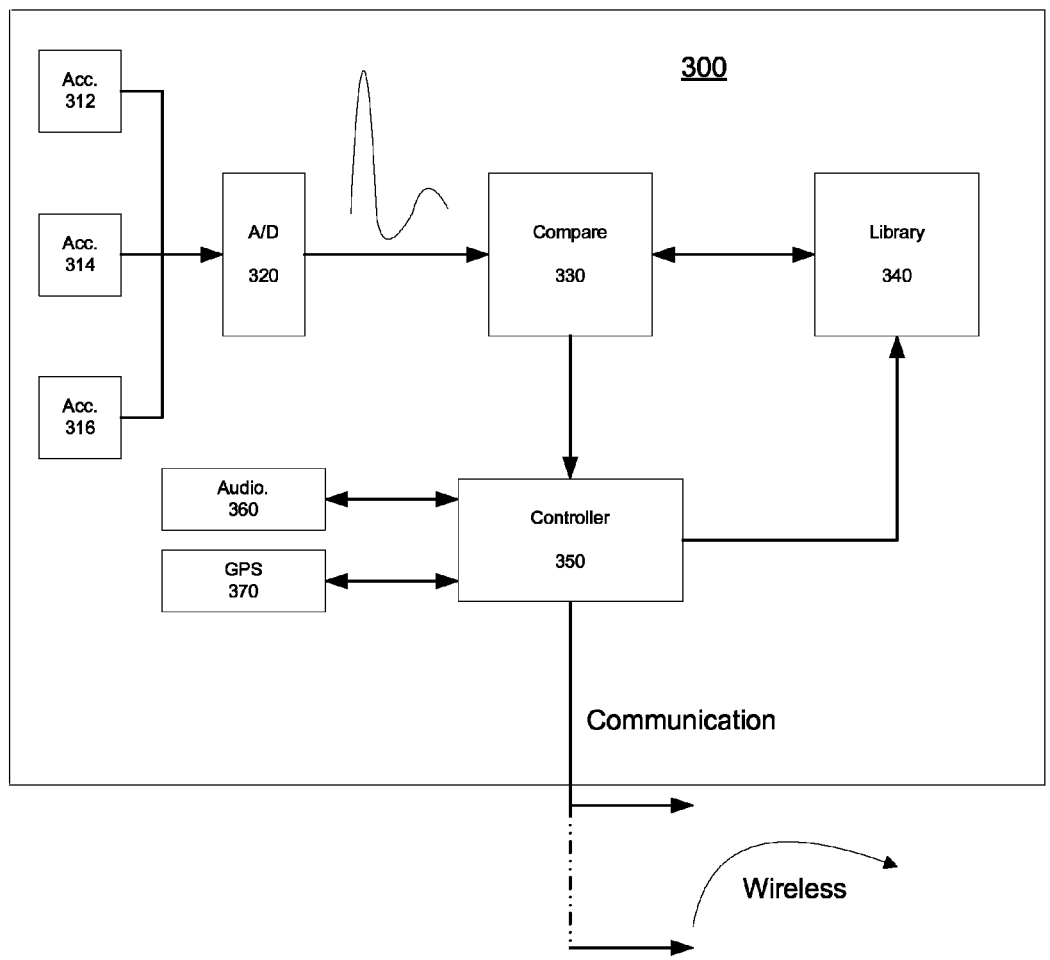
FIG. 3 is an example of a block diagram of a motion detection device.

FIG. 3 is an example of a block diagram of a motion detection device. The motion detection device can be attached to an object, and therefore, detect motion of the object that can be identified. Based on the identified motion, estimates of the behavior and conditions of the object can be determined.

The motion detection device includes sensors (such as, accelerometers) that detect motion of the object. One embodiment of the sensors includes accelerometers 312, 314, 316 that can sense, for example, acceleration of the object in X, Y and Z directional orientations. It is to be understood that other types of motion detection sensors can alternatively be used.

An analog to digital converter (ADC) digitizes analog accelerometer signals. The digitized signals are received by compare processing circuitry 330 that compares the digitized accelerometer signals with signatures that have been stored within a library of signatures 340. Each signature corresponds with a type of motion. Therefore, when a match between the digitized accelerometer signals and a signature stored in the library 340, the type of motion experienced by the motion detection device can determined.

An embodiment includes filtering the accelerometer signals before attempting to match the signatures. Additionally, the matching process can be made simpler by reducing the possible signature matches.

An embodiment includes identifying a previous human activity context. That is, for example, by knowing that the previous human activity was walking, certain signatures can intelligently be eliminated from the possible matches of the present activity that occurs subsequent to the previous human activity (walking).

An embodiment includes additionally reducing the number of possible signature matches by performing a time-domain analysis on the accelerometer signal. The time-domain analysis can be used to identify a transient or steady-state signature of the accelerometer signal. That is, for example, a walk may have a prominent steady-state signature, whereas a fall may have a prominent transient signature. Identification of the transient or steady-state signature of the accelerometer signal can further reduce or eliminate the number of possible signature matches, and therefore, make the task of matching the accelerometer signature with a signature within the library of signature simpler, and easier to accomplish. More specifically, the required signal processing is simpler, easier, and requires less computing power.

Upon detection of certain types of motion, an audio device 360 and/or a global positioning system (GPS) 370 can engaged to provide additional information that can be used to determine the situation of, for example, a human being the motion detection device is attached to.

The condition, or information relating to the motion detection device can be communicated through a wired or wireless connection. A receiver of the information can process it, and make a determination regarding the status of the human being the motion detection device is attached to.

Figure 4:
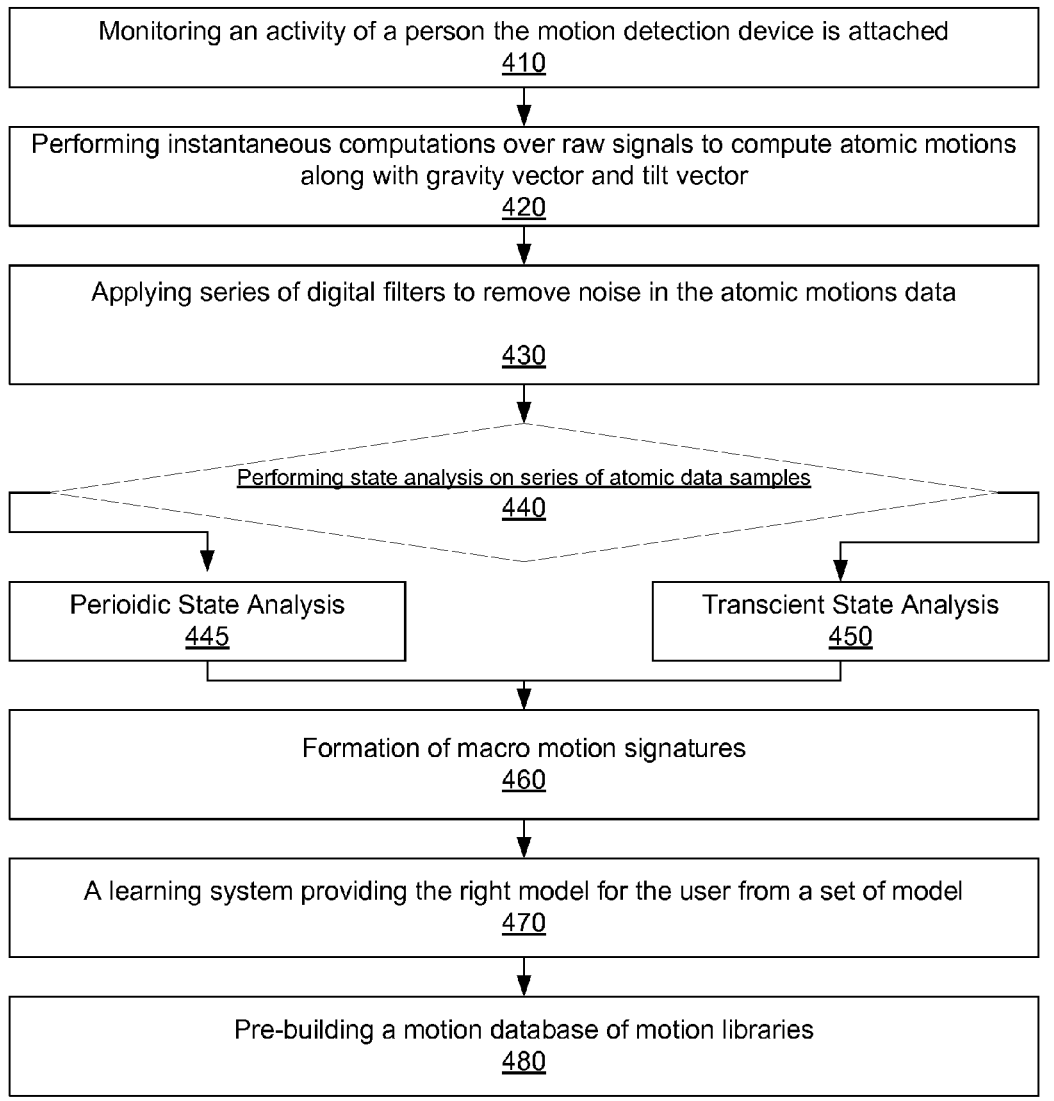
FIG. 4 is a flowchart that includes the steps of an example of a method for detecting various motions of daily living activities and emergency situations, such as, a fall.

FIG. 4 is a flowchart that includes the steps of an example of a method for detecting various motions of daily living activities and emergency situations, such as, a fall. A first step 410 includes monitoring an activity of a person the motion detection device is attached. Raw signal data is collected from, for example, an accelerometer sensor. A second step 420 includes performing instantaneous computations over raw signals to compute atomic motions along with gravity vector and tilt vector. A step third step 430 includes applying series of digital filters to remove noise in the atomic motions data. A fourth step 440 includes performing state analysis on series of atomic data samples and forming context. Depending on the state analysis, the series of atomic data is passed through either a step 445 periodic or steady state data analysis or a step 450 transient state data analysis. A sixth step 460 includes formation of macro motion signatures. The macro motion signatures are built from an output of state analysis vectors using known wavelet transformation techniques (for example, a Haar Transform). The transform performs pattern matching on current motion pattern with existing motion pattern library using, for example, DWT (Discreet Wavelet Transform) techniques. Complex motion wavelets are later matched using statistical pattern matching techniques, such as, HHMM (Hidden Heuristic Markov Model). The statistical pattern matching includes detecting and classifying events of interest. The events of interest are built by observing various motions and orientation states data of an animate or inanimate object. This data is used to train the statistical model which performs the motion/activity detection. Each activity will have its own model trained based on the observed data. A seventh step 470 includes a learning system providing the right model for the user from a set of model. It also aids in building newer (personal) patterns which are not in the library for the person who is wearing the motion detection device. An eighth step 480 includes pre-building a motion database of motion libraries against which motion signatures are compared. The database adds new motion/states signature dynamically as they are identified.

Figure 5:
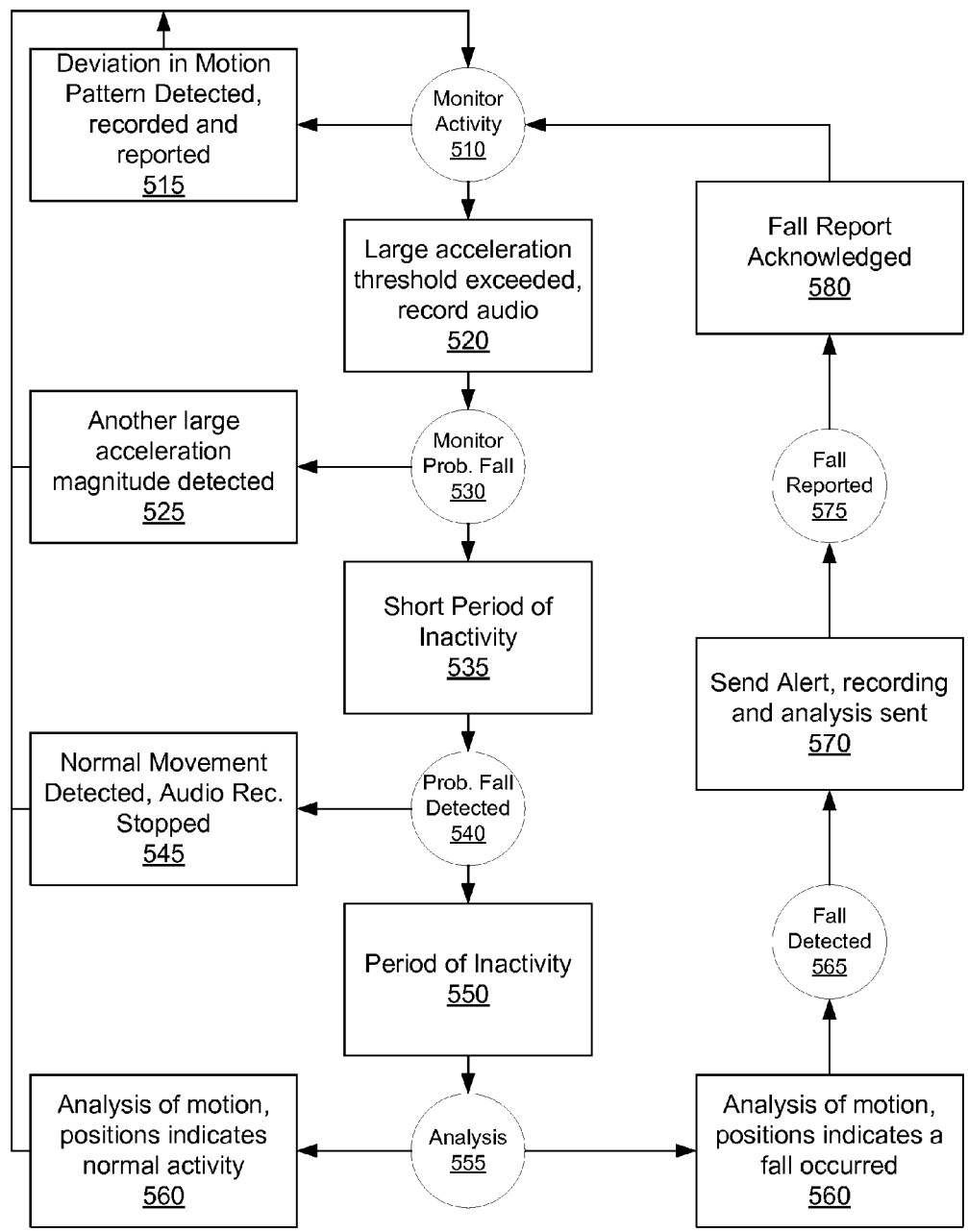
FIG. 5 is a flowchart that includes the steps of a method for detection of a fall.

FIG. 5 is a flowchart that includes the steps of an example of a method for detecting a fall. A first step 510 includes monitoring an activity of, for example, a person the motion detection device is attached to. A step 515 includes recording and reporting in deviations in normal motion patterns of the person. A step 520 includes detecting the acceleration magnitude deviation exceeding a threshold. The acceleration magnitude deviation exceeding the threshold can be sensed as a probable fall, and audio recording is initiated. Upon detection of this condition, sound recording of the person the motion detection device is connected to can be activated. The activation of sound can provide additional information that can be useful in assessing the situation of the person. A step 530 includes monitoring the person after the probable fall. A step 525 includes detection of another acceleration having magnitude lesser than the threshold, and continuing monitoring of audio. A step 535 includes detecting a short period of inactivity. A step 540 includes monitoring the person after determining a fall probably occurred. A step 545 includes subsequently detecting normal types of motion and turning off the audio because the person seems to be performing normal activity. A step 550 includes monitoring a period of inactivity. A step 555 includes additional analysis of detected information and signals. A step 560 includes further analysis including motion data, orientation detection all indicating the person is functioning normally. A step 560 includes determining that a fall has occurred based on the analysis of the motion data, and analysis of a concluded end position and orientation of the person. The sound recording can be de-activated. A step 565 includes concluding that a fall has occurred. A step 570 includes sending an alert and reporting sound recordings. A step 575 includes the fall having been reported. A step 580 includes an acknowledgement of the fall.

Figure 6:
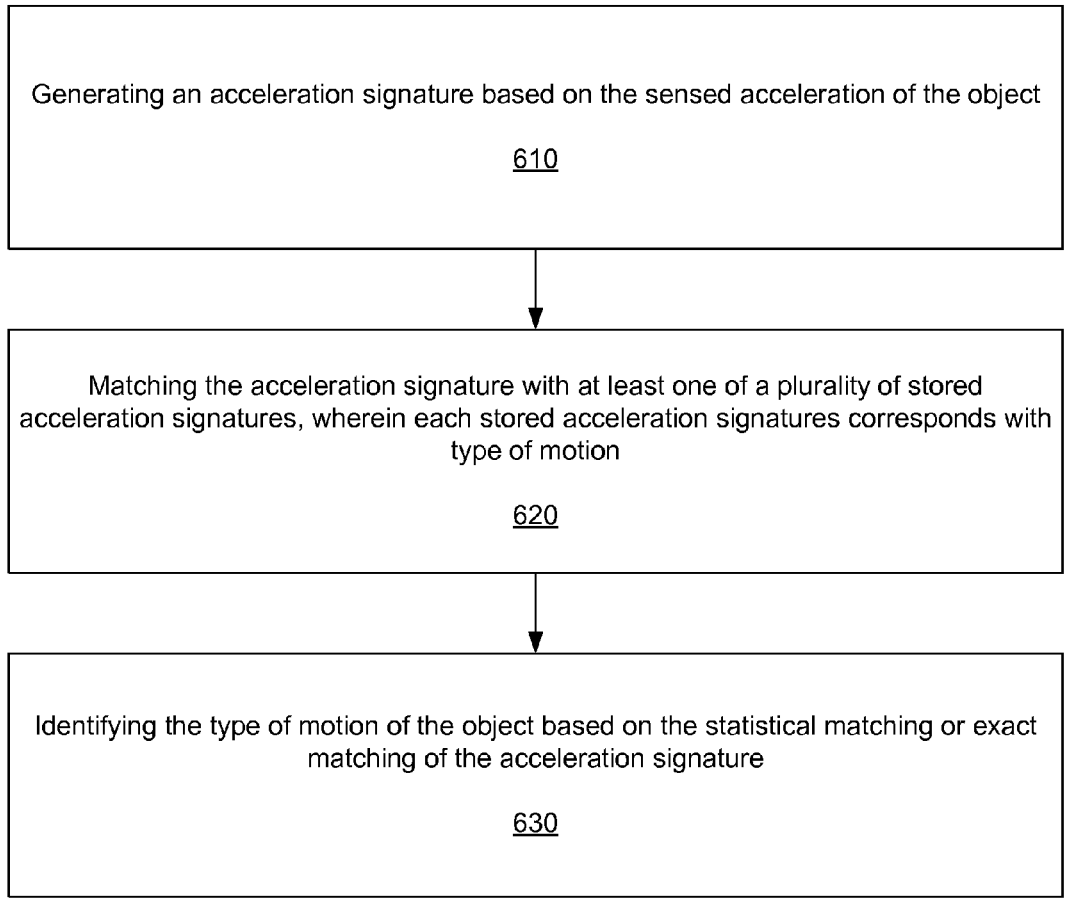
FIG. 6 is a flow chart that includes the steps of one example of a method of identifying a type of motion of an animate or inanimate object.

FIG. 6 is a flow chart that includes the steps of one example of a method of identifying a type of motion of an animate or inanimate object. A first step 610 includes generating an acceleration signature (for example, a tri-axial) based on the sensed acceleration of the object. A second step 620 includes matching the acceleration signature with at least one of a plurality of stored acceleration signatures, wherein each stored acceleration signatures corresponds with type of motion. A third step 630 includes identifying the type of motion of the object based on the statistical (pattern) matching or exact matching of the acceleration signature. As will be described, the acceleration signal can be created using a wavelet transformation.

For embodiments, the type of motion includes at least one of atomic motion, elemental motion and macro-motion.

Though embodiments of generating matching acceleration signatures are described, it is to be understood that additional or alternate embodiments can include generating and matching of orientation and/or audio signatures. Correspondingly, the first step 610 can include generating an acceleration signature, (and/or) orientation and audio signature based on the sensed acceleration, orientation of the object and audio generated by the object, for example, a thud of a fall, or a cry for help.

Atomic motion includes but is not limited to a sharp jolt, a gentle acceleration, complete stillness, a light acceleration that becomes stronger, a strong acceleration that fades, a sinusoidal or quasi-sinusoidal acceleration pattern, vehicular acceleration, vehicular deceleration, vehicular left and right turns, and more.

Elemental motion includes but is not limited to motion patterns for walking, running, fitness motions (e.g. elliptical machine exercises, rowing, stair climbing, aerobics, skipping rope, bicycling . . . ), vehicular traversal, sleeping, sitting, crawling, turning over in bed, getting out of bed, getting up from chair, and more.

Macro-motion includes but is not limited to going for a walk in the park, leaving home and driving to the shopping center, getting out of bed and visiting the bathroom, performing household chores, playing a game of tennis, and more.

Each of the plurality of stored acceleration signatures corresponds with a particular type of motion. By matching the detected acceleration signature of the object with at least one of a plurality of stored acceleration signatures, an estimate or educated guess can be made about the detected acceleration signature.

An embodiment includes a common library and a specific library, and matching the acceleration signature includes matching the acceleration signature with stored acceleration signatures of the common library, and then matching the acceleration signature with stored acceleration signatures of the specific library. For a particular embodiment, the general library includes universal acceleration signatures, and the specific library includes personal acceleration signatures. That is, for example, the stored acceleration signatures of the common library are useable for matching acceleration signatures of motions of multiple humans, and the stored acceleration signatures of the specific library are useable for matching acceleration signatures of motions of a particular human. Additionally, each library can be further categorized to reduce the number of possible matches. For example, at an initialization, a user may enter physical characteristics of the user, such as, age, sex and/or physical characteristics (such as, the user has a limp). Thereby, the possible signatures matches within the general library can be reduced. The signature entries within the specific library can be learned (built) over time as the human wearing the motion detection device goes through normal activities of the specific human. The specific library can be added to, and improved over time.

An embodiment includes filtering the acceleration signals. Additional embodiment include reducing the number of stored acceleration signature matches by identifying a previous activity of the object, and performing a time domain analysis on the filtered acceleration signal to identify transient signatures or steady-state signatures of the filtered acceleration signal. That is, by identifying a previous activity (for example, a human walking of sleeping) the possible number of present activities can be reduced, and therefore, the number of possible stored acceleration signature matches reduced. Additionally, the transient and/or steady-state signatures can be used to reduce the number of possible stored acceleration signature matches, which can improve the processing speed.

Another embodiment includes activating audio sensing of the object if matches are made with at least portions of particular stored acceleration signatures. For example, if the acceleration signature exceeds a threshold value, then audio sensing of the object is activated. This is useful because the audio information can provide additional clues as to what, for example, the condition of a person. That is, a fall may be detected, and audio information can be used to confirm that a fall has in fact occurred.

Another embodiment includes transmitting the sensed audio. For example, of a user wearing the object has fallen, and the fall has been detected, audio information can be very useful for determining the condition of the user. The audio information can allow a receiver of the audio information to determine, for example, if the user is in pain, unconscious or in a dangerous situation (for example, in a shower or in a fire).

An embodiment includes the object being associated a person, and the stored acceleration signatures corresponding with different types of motion related to the person. A particular embodiment includes identifying an activity of the person based on a sequence of identified motions of the person. The activity of the person can include, for example, falling (the most important in some applications), walking, running, driving and more. Furthermore, the activities can be classified as daily living activities such as walking, running, sitting, sleeping, driving, climbing stairs, and more, or sporadic activities, such as falling, having a car collision, having a seizure and so on.

An embodiment includes transmitting information related to the identified type of motion if matches are made with particular stored acceleration signatures. The information related to the identified type of motion can include at least one of motions associated with a person the object is associated with. The motions can include, for example, a heartbeat of the person, muscular spasms, facial twitches, involuntary reflex movements which can be sensed by, for example, an accelerometer. Additionally, the information related to the identified type of motion can include at least one of location of the object, audio sensed by the object, temperature of the object.

Another embodiment includes storing at least one of the plurality of stored acceleration signatures during an initialization cycle. The initializing cycle can be influenced based on what the object is attached to. That is, initializing the stored acceleration signatures (motion patterns) can be based on what the object is attached to, which can both reduce the number of signatures required to be stored within, for example, the general library, and reduce the number of possible matches and reduce the processing required to identify a match. Alternatively or additionally, initializing the stored acceleration signatures can be based on who the object is attached to, which can influence the specific library. The initialization can be used to determine motions unique, for example, to an individual. For example, a unique motion can be identified for a person who walks with a limp, and the device can be initialized with motion patterns of the person walking with a limp.

An embodiment includes initiating a low-power sleep mode of the object if sensed acceleration is below a threshold for a predetermined amount of time. That is, if, for example, a person is sensed to be sleeping, power can be saved by de-activating at least a portion of the motion sensing device.

Figure 7:
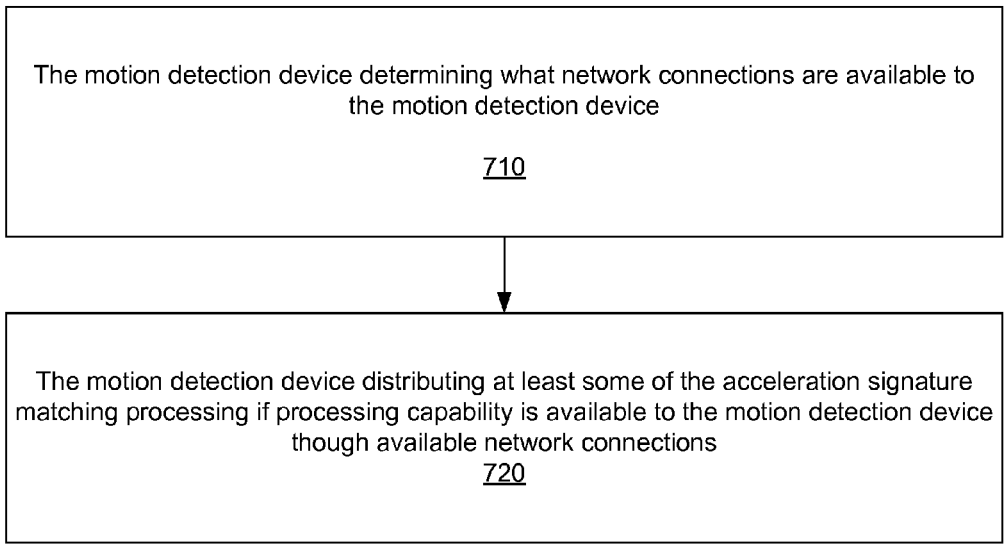
FIG. 7 is a flow chart that includes steps of one example of a method of a motion detection device checking network availability for improvements in speed and/or processing power of acceleration signature matching.

FIG. 7 is a flow chart that includes steps of one example of a method of a motion detection device checking network availability for improvements in speed and/or processing power of acceleration signature matching, wherein the motion detection device includes motion detection sensors that generate the acceleration signal. A first step 710 includes the motion detection device determining what network connections are available to the motion detection device. A second step 710 includes the motion detection device distributing at least some of the acceleration signature matching processing if processing capability is available to the motion detection device though available network connections.

For an embodiment, the motion detection device distributes the acceleration signature matching processing if the processing capability is available to the motion detection device though available network connections, and distributing the acceleration signature matching processing saves the motion detection device processing power. Another embodiment, the motion detection device distributes the acceleration signature matching processing if the processing capability is available to the motion detection device though available network connections, and distributing the acceleration signature matching processing increases a speed of the motion detection device processing. Alternatively, the motion detection device distributes the processing to optimize both power and processing speed. Additionally, the processing distribution can be dependent upon the bandwidths of the available network connections. That is, some networks connections can generally support higher data transfer rates, and therefore, influence the processing speed.

Generally, the motion detection device scales its processing to the level of processing available. That is, as additional processing power becomes available to the motion detection device, the motion detection device can increase the complexity of the signature matching processing. The processing can be distributed as processing capability becomes available through network connections. The processing can be performed in different locations as network connectivity becomes available, which can advantageously reduce the power consumption of the motion detection device and/or increase the speed of the processing.

Figure 8:
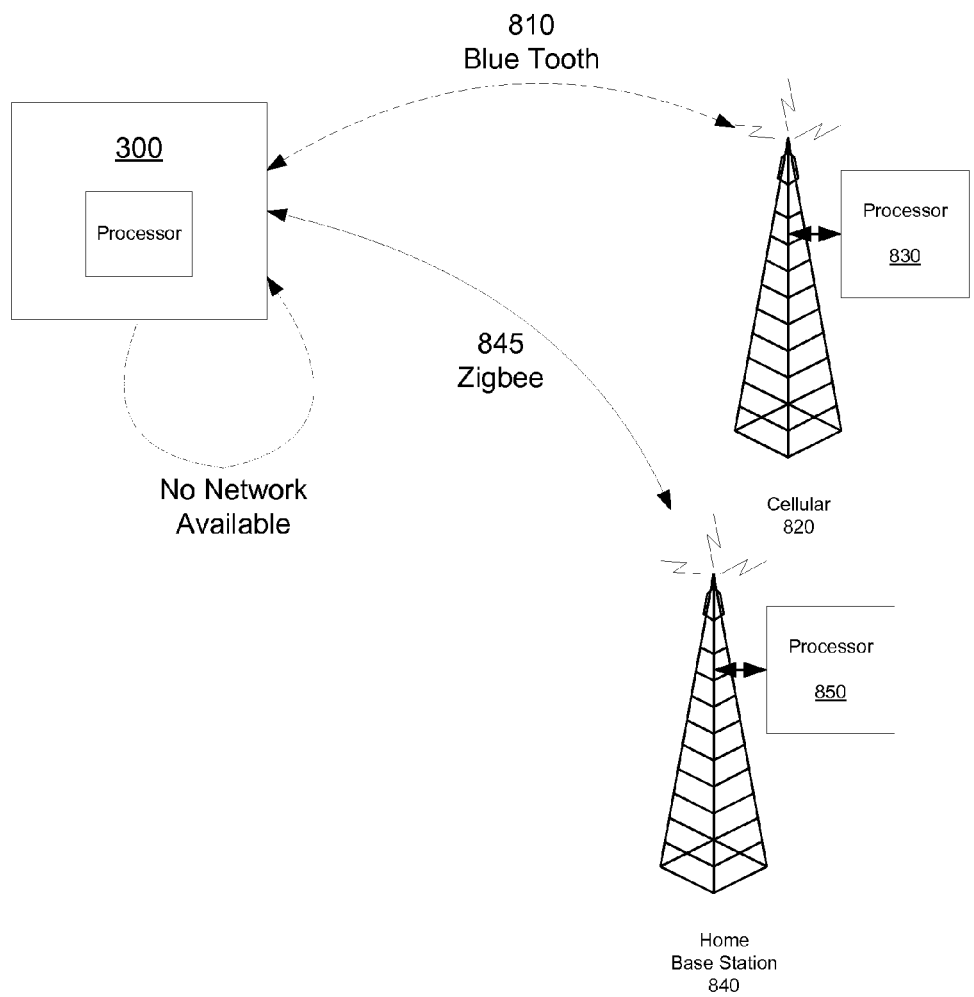
FIG. 8 shows a motion detection device that can be connected to one of multiple networks.

FIG. 8 shows a motion detection device 300 that can be connected to one of multiple networks. Examples of possible networks (not a comprehensive list) the motion detection device 300 can connect to, include a cellular network 820 through, for example, a blue tooth wireless link 810, or to a home base station 840 through, for example, a Zigbee wireless link 845. The wireless links 810, 845 can each provide different levels of bandwidth. Each of the networks includes available processing capabilities 830, 850.

If the motion detection device 300 does not have any network connections available, the motion detection device 300 must perform its own matching processing. If this is the case, then the processing algorithms may be less complex to reduce processing power, and/or reduce processing speed. For example, the matching processing can be made simpler by comparing threshold levels for elemental motions by extracting significant wavelet coefficients. Acceleration signals data acquisition is performed in chunk of processing every few mili-seconds by waking up. For all other times the processor rests in low-power mode. Except for the emergency situation, the RF communication is done periodically when the data is in steady state, there is no need to send it to network i.e. when the object is in sedentary there is no need to send data change in the state is communicated to network. Additionally, if no network connections are available, the operation of the motion detection device 300 may be altered. For example, if the motion detection device 300 detects an emergency situation (such as, a fall), the motion detection device 300 may generate an audio alert. If a network connection was available, the audio alert may not be generated, but an alert may be transmitted over the available network.

The motion detection device 300 includes a processor in which at least a portion of the analysis and signature matching can processing can be completed. However, if the motion detection device 300 has one or more networks available to the motion detection device 300, the motion detection device can off-load some of the processing to one of the processors 730, 750 associated with the networks.

The determination of whether to off-load the processing can be based on both the processing capabilities provided by available networks, and the data rates (bandwidth) provided by each of the available networks.

Although specific embodiments have been described and illustrated, the embodiments are not to be limited to the specific forms or arrangements of parts so described and illustrated.

What is claimed:

1. A method of detecting human condition and activity of a user, comprising:
    generating, by a motion detection device that includes a motion detection sensor, an acceleration signature based on sensed acceleration of an object that represents motion of the user;
    the motion detection device determining what network connections are available to the motion detection device;
    matching the acceleration signature with at least one of a plurality of stored acceleration signatures of motions of human beings, wherein each stored acceleration signatures corresponds with a type of motion, wherein the motion detection device distributes at least some of the acceleration signature matching processing when processing capability is available to the motion detection device though available network connections;
    identifying a type of motion of the user and identifying a condition of the user based on the matching of the acceleration signature with a stored acceleration signature.

2. The method of claim 1, wherein the type of motion comprises at least one of atomic motion, elemental motion and macro-motion.

3. The method of claim 1, wherein the stored acceleration signatures are stored in a common library and a specific library, and matching the acceleration signature comprises matching the acceleration signature with stored acceleration signatures of the common library, and then matching the acceleration signature with stored acceleration signatures of the specific library.

4. The method of claim 3, wherein the common library includes universal motion and activities acceleration signatures, and the specific library includes person acceleration signatures.

5. The method of claim 3, wherein the stored acceleration signatures of the common library are useable for matching acceleration signatures of motions of multiple humans, and the stored acceleration signatures of the specific library are useable for matching acceleration signatures of motions of a particular human.

6. The method of claim 1, wherein when matches are made with at least portions of particular stored acceleration signatures, then audio sensing of the object is activated.

7. The method of claim 1, wherein matching further comprises filtering the acceleration signature.

8. The method of claim 7, further comprising reducing a number of stored acceleration signature matches by identifying a previous activity of the user, and performing a time domain analysis on the filtered acceleration signal to identify transient signatures or steady-state signatures of the filtered acceleration signal.

9. The method of claim 1, wherein if the acceleration signature exceeds a threshold value, then audio sensing of the object is activated.

10. The method of claim 9, further comprising transmitting the sensed audio.

11. The method of claim 1, further comprising identifying an activity of the user based on a sequence of identified motions of the person.

12. The method of claim 1, further comprising transmitting information related to the identified type of motion when matches are made with particular stored acceleration signatures.

13. The method of claim 1, further comprising storing at least one of the plurality of stored acceleration signatures during an initialization cycle.

14. The method of claim 1, further comprising initiating a low-power sleep mode of the object when sensed acceleration is below a threshold for a predetermined amount of time.

15. The method of claim 1, wherein the motion detection device distributes the acceleration signature matching processing when the processing capability is available to the motion detection device through available network connections, and distributing the acceleration signature matching processing saves the motion detection device processing power.

16. The method of claim 1, wherein the motion detection device distributes the acceleration signature matching processing when the processing capability is available to the motion detection device through available network connections, and distributing the acceleration signature matching processing increases a speed of the motion detection device processing.

17. An apparatus for identifying a type of motion and condition of a user, comprising:
   a motion detection sensor operative to generate an acceleration signature based on sensed acceleration of the user;
   a controller, wherein the controller is operative to:
      determine what network connections are available to the motion detection device;
      match the acceleration signature with at least one of a plurality of stored acceleration signatures, wherein each stored acceleration signatures corresponds with a type of motion of the user, wherein the apparatus distributes at least some of the acceleration signature matching processing when processing capability is available to the motion detection device though available network connections;
      identify the type of motion of the user and identify a condition of the user based on the matching of the acceleration signature.

18. The apparatus of claim 17, wherein the type of motion comprises at least one of atomic motion, elemental motion and macro-motion.

19. The apparatus of claim 17, wherein the stored acceleration signatures are stored in a common library and a specific library, and matching the acceleration signature comprises matching the acceleration signature with stored acceleration signatures of the common library, and then matching the acceleration signature with stored acceleration signatures of the specific library.

20. The apparatus of claim 19, wherein the common library includes universal motion and activities acceleration signatures, and the specific library includes person acceleration signatures.

* * * * *